(12) United States Patent
Mattheck et al.

(10) Patent No.: US 6,290,437 B1
(45) Date of Patent: Sep. 18, 2001

(54) BORE RESISTANCE MEASURING APPARATUS INCLUDING A DRIVE UNIT AND AN ATTACHMENT FOR A DRILL AND OR DRIVING MECHANISM

(75) Inventors: Claus Mattheck, Leimersheim; Erich Hunger, Wiesloch, both of (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/421,904

(22) Filed: Oct. 20, 1999

Related U.S. Application Data

(63) Continuation-in-part of application No. PCT/EP98/02385, filed on Apr. 24, 1998.

(30) Foreign Application Priority Data

Apr. 23, 1997 (DE) .......................................... 297 07 307 U

(51) Int. Cl.⁷ .............................. B23B 41/00; G01N 3/42
(52) U.S. Cl. .......................... 408/2; 73/81; 73/85; 408/11
(58) Field of Search .................. 73/78, 81, 85, 73/104; 408/2, 6, 8, 9, 11

(56) References Cited

U.S. PATENT DOCUMENTS

| | | | |
|---|---|---|---|
| 2,389,030 | * 11/1945 | Dana | 73/81 |
| 4,249,414 | * 2/1981 | Barth | 73/81 |
| 4,540,318 | * 9/1985 | Hornung et al. | 408/8 |
| 5,014,793 | * 5/1991 | Germanton et al. | 408/9 |
| 5,792,960 | * 8/1998 | Lewis | 73/81 |

FOREIGN PATENT DOCUMENTS

| | | |
|---|---|---|
| 35 01 841 | 4/1986 | (DE) . |
| 40 04 242 | 8/1991 | (DE) . |
| 41 22 494 | 3/1992 | (DE) . |
| 44 38 383 | 5/1996 | (DE) . |
| 0 673 723 | 9/1995 | (EP) . |
| 2 600 772 | 12/1987 | (FR) . |
| 2 242 029 | 9/1991 | (GB) . |

* cited by examiner

*Primary Examiner*—Daniel W. Howell
(74) *Attorney, Agent, or Firm*—Klaus J. Bach

(57) ABSTRACT

In a drill resistance measuring apparatus including a drive unit and an attachment for determining the internal state of trees or wooden structures by determining the torque required to drive a drill into the wood, means for plotting and storing the torque depending on the penetration depth of the drill are included in the drive unit attachment, which includes a coupling portion for coupling to the drive unit and a transmission mechanism exchangeably supported in the attachment to permit an exchange of the transmission mechanism for a change of the transmission ratio for operating the drill at various speeds.

11 Claims, 6 Drawing Sheets

BORE RESISTANCE MEASURING APPARATUS INCLUDING A DRIVE UNIT AND AN ATTACHMENT FOR A DRILL AND OR DRIVING MECHANISM

This is a continuation-in-part application of international application PCT/EP98/02385 filed Apr. 24, 1998.

BACKGROUND OF THE INVENTION

The invention relates to a bore resistance measuring apparatus comprising a drill attachment and a driving mechanism according to the preamble of claim 1, as it is known from DE-A-443 383.

In a method known as such (DE 35 018 41 C1) holes are drilled into objects which mainly consist of wood using a long needle-like drill wherein the penetration resistance is measured, recorded and/or electronically stored. From the resistance diagram determined in this way conclusions can be made concerning the inner structure of the test object for dendrochronological purposes, the determination of growth rates, the effects of diseases and the examination of load capacity.

The drills known so far which are operated by electric batteries include a drill motor which is movably supported on a sliding carriage which is movable along a slide track and where back-and-forward movement is effected by a drive motor via a screw or gear drive. Also, a drive arrangement has become known wherein the drive motor is also arranged on the slide carriage for the drill motor and moves itself by way of a pinion engaging a stationary spur rack. Before the long drill needle has entered the object to be examined up to a certain depth, the drill needle must be supported because otherwise it would form a vibration belly under the effect of the drill needle advancing force. Then tubes are used as support elements which move telescopically over one another as the drill needle is advanced.

Some apparatus models include recording devices in order to be able to control the drilling already while in progress. The plotting or recording devices may be arranged within the housing of the apparatus or at the outside thereof. Power is supplied from an external battery by way of a cable; but other apparatus are known wherein the battery is mounted to the housing of the drilling apparatus. Without exception, the known drilling apparatus include a tubular protective sleeve of angular or circular cross-section having a front end with an opening through which the drill needle extends and a rear end with a handle having switching, plug-and control elements and, within the tube, a guide track and the needle support elements.

The drill resistance measurement for tree and wood examinations has been widely used since it has become known. However, for a wider use, it is disadvantageous that the price for the examination equipment is relatively high; and the reason herefor, in turn, is that the equipment is needed in only small numbers so that it is not worthwhile to mass-produce the equipment.

The elements described which are needed for the method require of course a certain space in all three directions and also have a relatively high weight.

Since drill tests must be performed in many cases from locations which are difficult to access for example, among the branches of trees, at high ceilings in buildings while standing on ladders, or in attics which are difficult to access the equipment must often be held above the head and guided by hand. In the process, canting of the drill needle or a deviation from the direction of drilling must be avoided.

From DE-A-41 22 492, a drill resistance measurement apparatus is known with all these features wherein a planetary transmission cannot serve as a force receiver.

It is the object of the invention to provide a drill resistance measuring device with the smallest possible dimensions and the smallest possible weight which permits easy and safe handling and which can be manufactured at reasonably low costs.

SUMMARY OF THE INVENTION

In a drill resistance measuring apparatus including a drive unit and an attachment for determining the internal state of trees or wooden structures by determining the torque required to drive a drill into the wood, means for plotting and storing the torque depending on the penetration depth of the drill are included in the drive unit attachment, which includes a coupling portion for coupling to the drive unit and a transmission mechanism exchangeably supported in the attachment to permit an exchange of the transmission mechanism for a change of the transmission ratio for operating the drill at various speeds.

The apparatus for the drill resistance measurements basically have a number of analyses with electric hand drills. It has therefore already been proposed to basically use such a machine—which is available commercially expensively as compared to the drill resistance measuring apparatus—as the basic device and equip it with a supplemental attachment suitable for the particular object, as it is known for example, to use drills as pumps, grinders, sabre saws, screwdrivers, etc . . .

Such an apparatus, which is short is not only easy to handle but the leverage between the contact point with the object to be examined and the handle is so small that canting or undesirable movements during the drilling procedure have little negative effects.

The short design has been achieved by a combination of principles and design features. For example, in contrast to the commercially available equipment, besides the required drill motor, a particular advancing motor was omitted and the advance was achieved by suitable design features of the hand drill as will be described below in detail.

In a known proposal (DE 40 04 242 A1), the drilling and advancing is provided for by a single motor, but no design solution is shown herefor beyond the statement that reducing transmission is used which is matter of course. Such a design would be relatively simple with this proposal since the drill motor is disposed on the advancement carriage, which it could drive by way of a second shaft stub.

The present invention accommodates the drilling as well as the advancing by a motor, which is arranged outside the actual drilling device, that is, in the hand drill. The energy transmission for the drilling as well as for the advancing is achieved solely mechanically.

Since, as a result, the actual drilling device does not include any motors, switches or sensors, there are also no electrical installations or cables, loop cables, current tracks, switches or plugs which facilitates, and permits, inexpensive assembly.

An embodiment of the invention will be described in greater detail below on the basis of the drawings.

DESCRIPTION OF A PREFERRED EMBODIMENT

Figure 1:
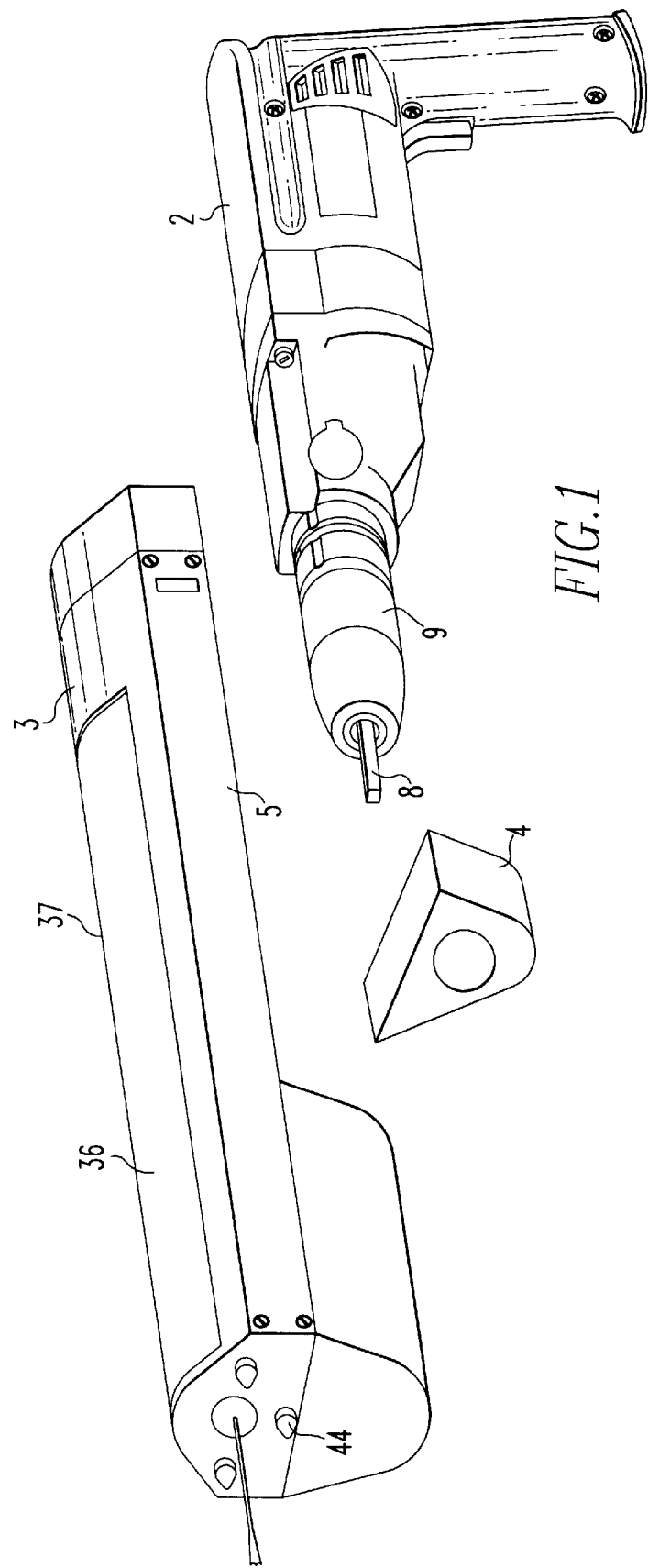
FIG. 1 shows a commercially available drill as a drive unit with a drill attachment.
Figure 2:
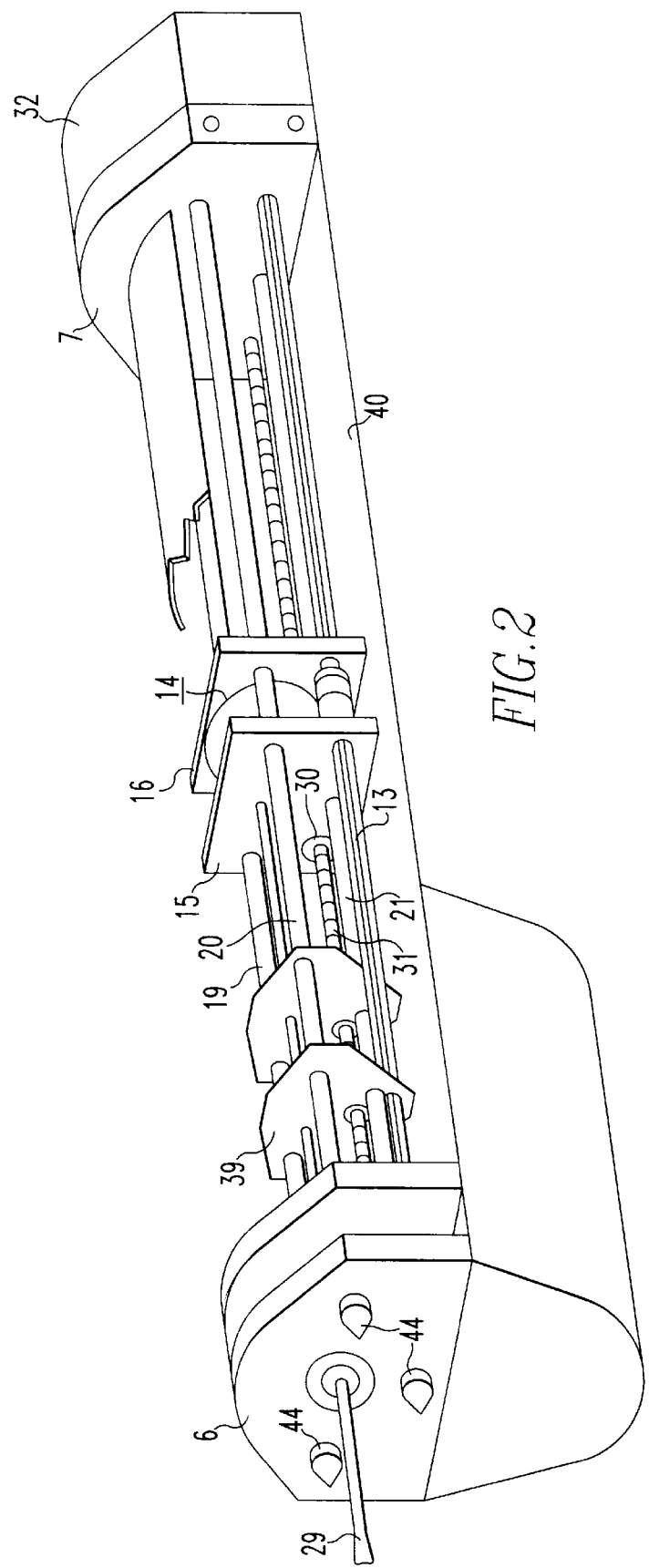
FIG. 2 shows schematically a drill attachment.
Figure 3:
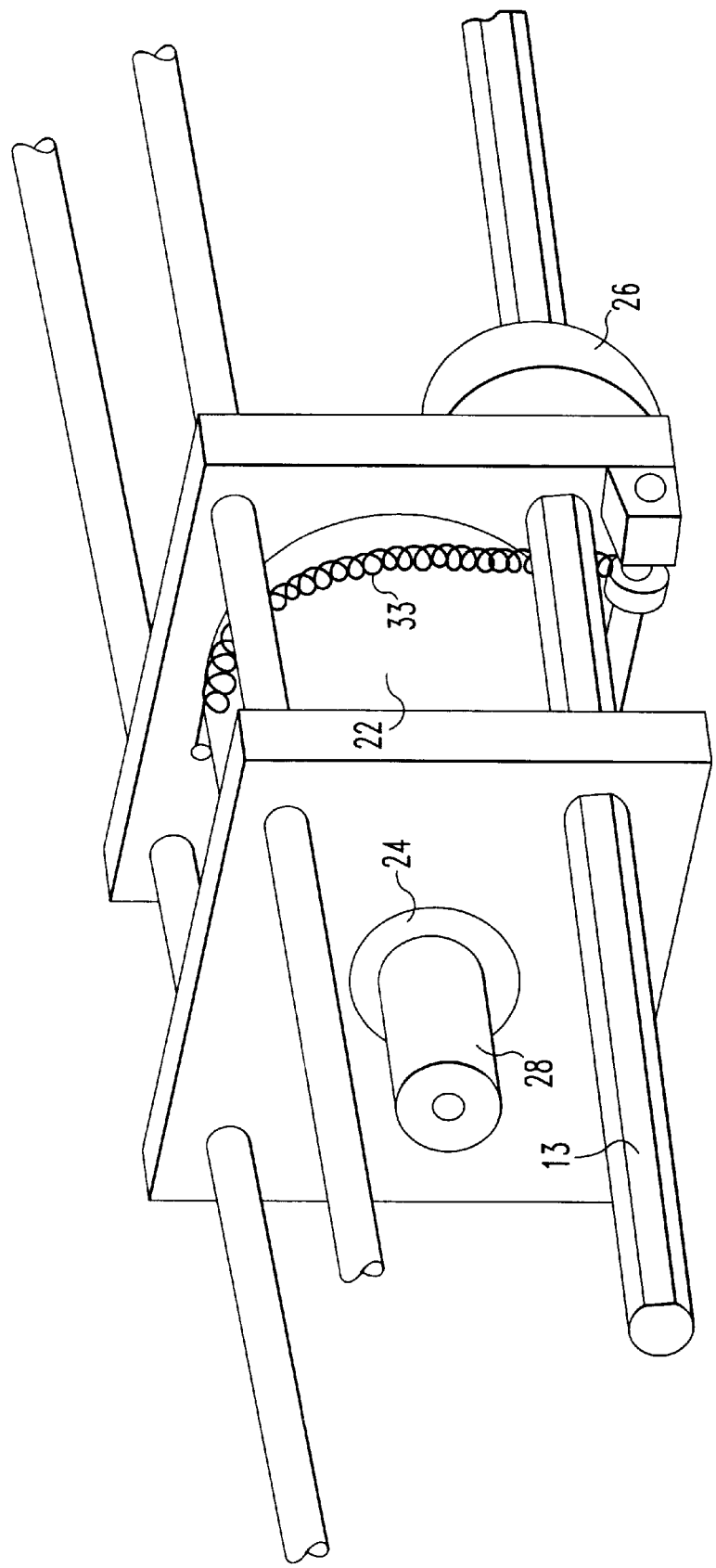
FIG. 3 shows the carriage, which is slideable on the drill attachment on which the drill needle is mounted.
Figure 4:
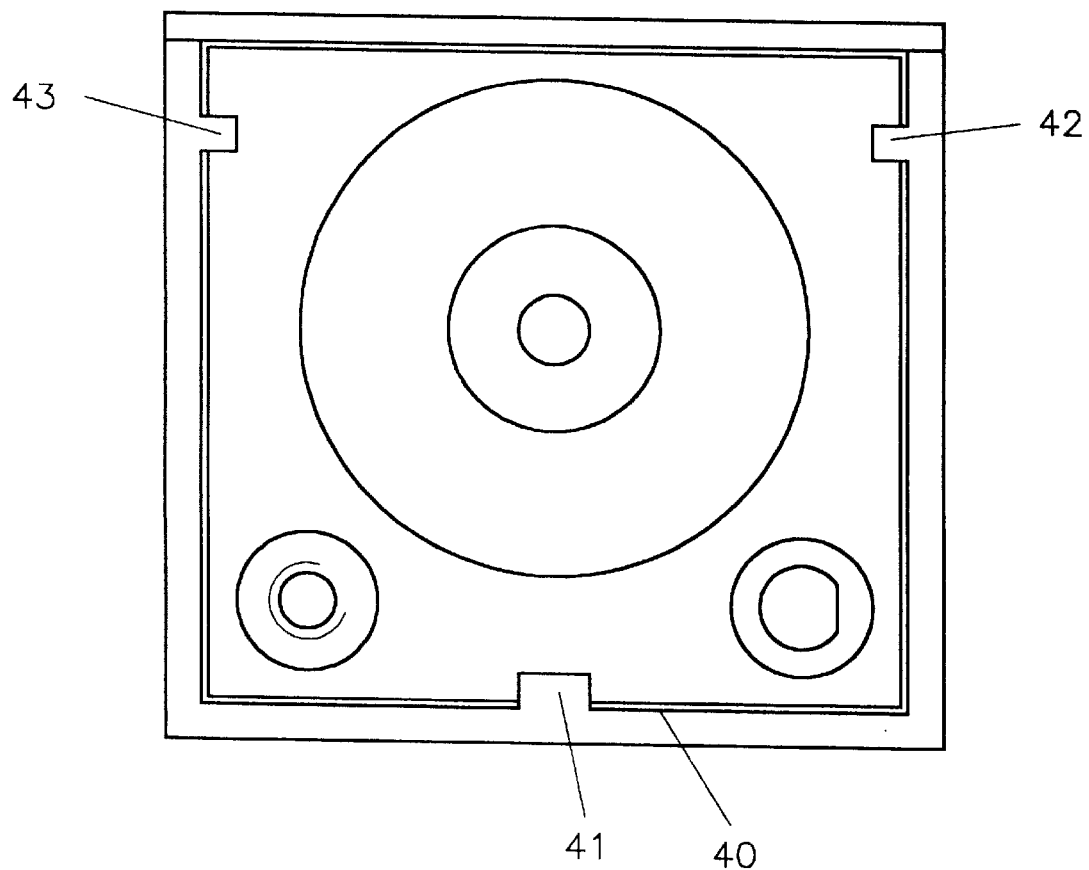
FIG. 4 shows, in cross-section, a particular embodiment of the tubular body wherein the slide bars are replaced by guide strips.
Figure 5:
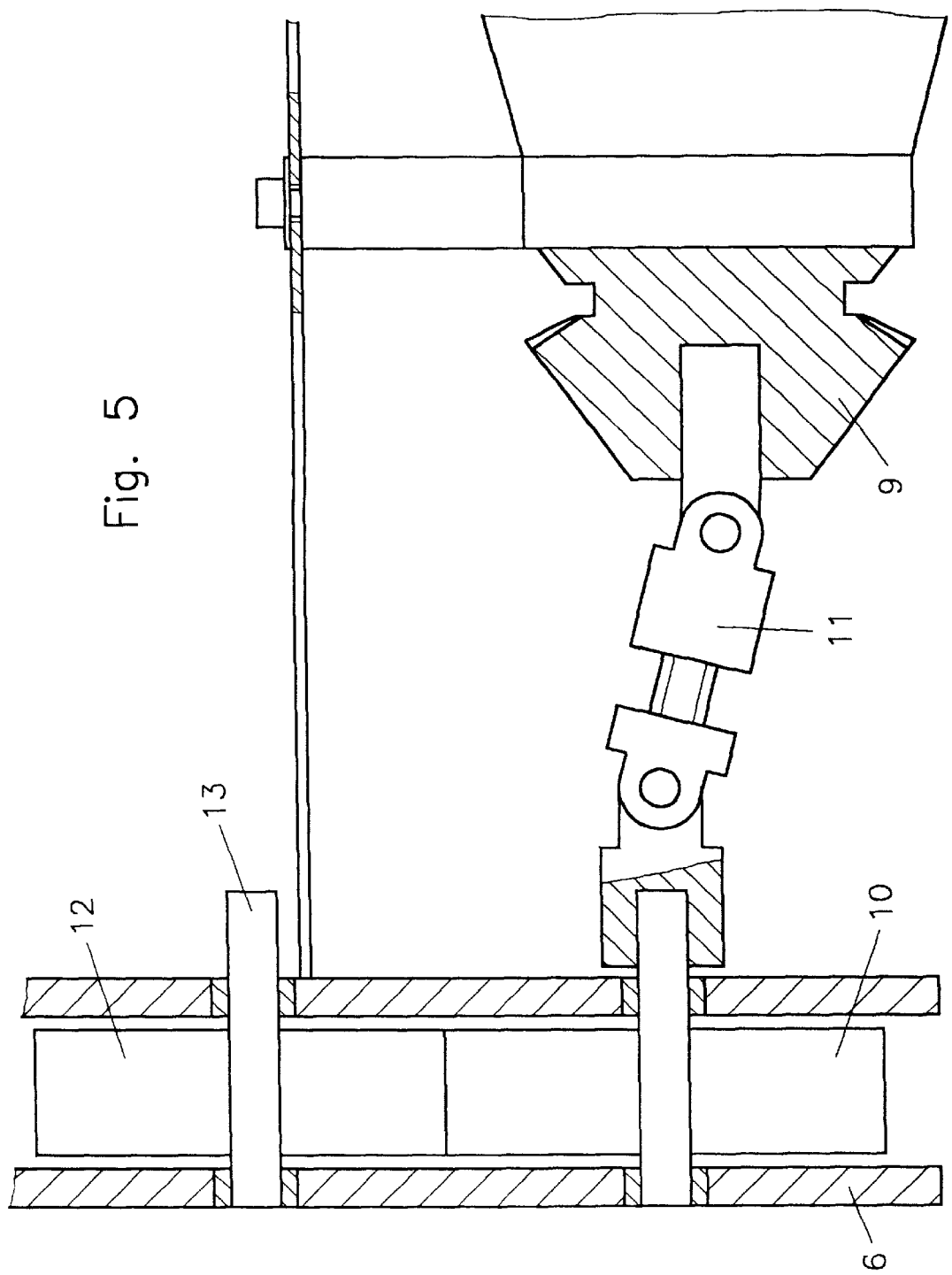
FIG. 5 shows the coupling between the drill and the drill attachment.
Figure 6:
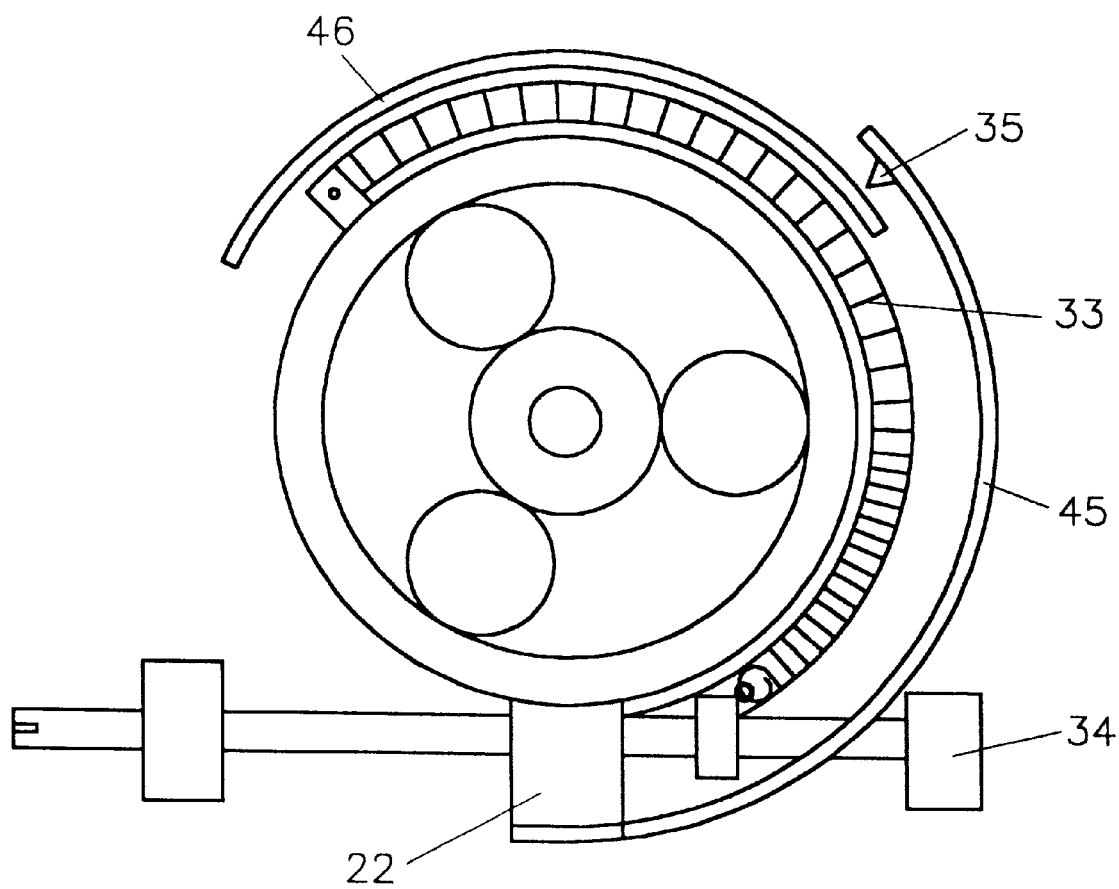
FIG. 6 shows the planetary transmission with a mechanical recording system.

The purely mechanical recording system of the drill resistance according to the invention, which will be described below in detail, has a better resolution capability than electrically operating recording systems installed in the apparatus. The reason herefor is that the electrically operating system operates with a certain energy consumption and a certain damping factor.

As a result of the design described earlier in principle and to be described in detail below, a drill resistance measuring apparatus is provided which is convenient and can easily be handled and which is inexpensive to manufacture when compared with prior art apparatus.

The novel features are specifically as described below:

For the drill resistance measuring apparatus 1, a commercially available hand drill 2 is used as the drive unit. The drill may be operated from a power supply or it may be provided with a battery so that it can be operated independently of a net. Such drills today generally include a mechanical or an electrical control arrangement for operation at different speeds, as well as a switch for forward or reverse rotation. It is advantageous for the proposed application that the various manufactures of such electric drills make the drills with almost identical dimensions in order to be able to use the same batteries or the same attachments or to mount a second additional handle on the drill. The drill attachment 3 is therefore so designed that it can be easily attached in a form-fitting manner to a large selection of different drills. Where this is not possible, an adapter 4 is utilized whose upper side is designed for a form fitting connection with the drill attachment and whose lower side is designed for a form-fitting connection to the respective drill 2 as used.

As the drive unit for example an electric motor or a pneumatically or hydraulically operated motor may be used. The drill attachment 3 comprises a tubular body 5, which, at its operating end, includes a front section 6 and at its opposite end has a cover section 7. They are combined by screwing, by cementing, by welding or by any other connecting system so as to form together a housing.

The transmission of the energy (the torque) from the drill 2 to the drill attachment is by way of a profiled shaft 8, which has a polygonal, preferably triangular, cross-section and on which the drill chuck 9 of the drill 2 is mounted.

The profiled shaft is inserted into a coupling portion so that the rotation of the drill 2 is transferred to a drive wheel 12 supported on the front section 6. From there, a main drive shaft 13 is driven, by way of a transmission mechanism in the form of either a gear/gear or a toothed belt drive, or a chain drive, or a V-belt drive. The main drive shaft is supported at one side on the front section 6 and, on the other side, in the cover section 7. The main drive shaft 13 includes either a flat surface area or a groove so that its rotation can be transmitted to a drive gear 26 longitudinally slideably supported on the main drive shaft 13.

The tubular body 5 has a carriage 14 slideably supported therein. It consists of a front plate 13 and a rear plate 16, which are screwed to the carriage housing by spacer members which are not shown. The spacer member may be in the form of tubes and, in this way, serve as slide sleeves for the carriage by way of which the carriage can be moved back and forth on the slide bars 19, 20, 21.

The slide bars 19, 20, 21 can be omitted if the tubular body 5 is so shaped that the carriage 14 slides on the bottom surface 40 and is guided by guide strips 41 and the plates 15, 16 have correspondingly formed cut-outs. The tubular body consists in this case preferably of plastic or a profiled aluminum strand.

A planetary transmission 22 is supported with its driven shaft on the rear plate 16 and with its drive shaft 24 on the front plate. The driven shaft which projects from the back of the carriage, carries a gear (not shown), which is in engagement with a drive gear 26 supported on the rear plate. It includes a bearing stub, which has a profiled bore corresponding to the profile of the main drive shaft 13. The drive gear 26 is therefore moved with the carriage as it is moved back and forth on the drive shaft 13 while it is rotated thereby. With the different diameters of this gear and the drive gear 26, a transmission effect is being realized.

The drive shaft 24 of the planetary transmission is provided with a mounting structure 28 for form-fittingly receiving the drill needle 29, which mounting structure is preferable a scroll or a clamping chuck.

The back and forth movement of the carriage is achieved by a worm 30 which is firmly installed in the housing of the carriage 14 and on which the threaded spindle 31 acts. The spindle 31 again is supported by the front section 6 and the cover section 7 and is rotated by a variable ratio transmission 32, which again is mounted on the outside of the cover section 7, by the main drive shaft 13.

The variable ratio transmission 32 is so designed that differently grouped gears are arranged in cassettes, which can be selectively inserted into the transmission housing whereby the transmission ratio between the main drive shaft 13 and the threaded spindle 31 can be changed as desired.

The housing of the planetary transmission 22 disposed in the carriage is not rigidly connected to the carriage, but is supported by an appropriate support structure so as to be freely pivotable between the plates 15 and 16. The reaction torque of the drive for the drill needle effective on the housing is accommodated by a tension or compression spring 33, which is mounted with one end to the housing of the planetary transmission 22. The opposite end is mounted to the carriage 14 by way of a screw mechanism 34 for adjusting the spring tension. The spring force of the spring 33 can be changed by a suitable mechanism. As a result, the apparatus can be set for differently hard materials. Attached to the housing of the planetary transmission is a recording mechanism 34 which records the changes of the reaction torque on a register paper strip 36. The strip is inserted into the drill attachment through a flap window 37 at the upper side of the drill attachment 3 and is held in position by a suitable clamping structure—which is not shown.

Since the writing pen 35 is advanced together with the carriage at the rate at which the drill needle enters, a graph is generated, which indicates for each point of the drill advance the torque applied during the drilling. It is at the same time a measure for the respective density of the body examined.

Instead of, or in addition to, a mechanically recorded curve, an electronic recording and/or storage may be performed. To this end, the threaded spindle 31 could be provided at the variable transmission 32 with a signal sensor which is known per se and by way of which the drilling progress is determined. The required torque may be determined and recorded in a known manner by way of an impulse sensor at the planetary transmission 22 or at a suitable location at the bearings of the main drive shaft 13 or by way of the current consumption of the drill 2.

In order to protect the apparatus from damage shear pins and/or slip clutches may be provided in a known manner.

The front section includes tips 44 in order to engage firmly the apparatus with the object being examined when the apparatus is firmly pressed against the object.

What is claimed is:

1. A drill resistance measuring apparatus consisting of a drill attachment and a drive unit for determining the internal state and the density of trees or wooden construction elements, said attachment including a housing, a thin drill needle rotatably and axially movably supported on said attachment, and means for plotting and means for recording the torque effective on the drill needle and the penetration depth of-the drill needle, said drill attachment being connected to said drive unit at one side thereof and having a coupling portion coupling said drive unit to said drill attachment, and said drill attachment having a front end with a transmission mechanism, a main drive shaft rotatably supported in said drill attachment, a drive gear longitudinally slideably supported on said main drive shaft so as to be rotated with said main drive shaft, and a transmission gear engaged by said drive gear for rotating said drill needle, said drill needle being rotatably supported on a carriage, and a threaded spindle mounted so as to provide, in cooperation with a worm in said carriage, for back and forth movement of the carriage, and a variable ratio transmission exchangeably disposed in said attachment so as to be operated by said drive unit to rotate said threaded spindle.

2. A drill resistance measuring apparatus according to claim 1, wherein said drill attachment comprises a housing having at one end thereof a tubular front section, and, toward the opposite end, a cover section, which are firmly interconnected.

3. A drill resistance measuring apparatus according to claim 2, wherein, for the transfer of the energy from the drive unit in the drill attachment, a profiled shaft is used which has a polygonal profile, a drive wheel is supported in the front section, and includes a coupling portion for receiving the profiled shaft, the main shaft is rotatably supported at one side in the front section and at the other side, in the cover section and a gear which is longitudinally slideably supported on said main shaft so as to be rotated with the main shaft and the transmission mechanism, thereby transmitting the rotation from the drive wheel to the main shaft.

4. A drill resistance measuring apparatus according to claim 2, wherein said carriage is slideably supported in said housing and consists of a front plate and a rear plate and spacers maintaining the two plates in spaced relationship, said spacers being tubes which form slide sleeves for the carriage, and are disposed on slide bars, which are mounted to the front section and the cover section.

5. A drill resistance measuring apparatus according to claim 3, wherein said housing consists of a plastic or aluminum profile having an inner bottom surface on which a carriage is slideably supported and guided by guide strips.

6. A drill resistance measuring apparatus according to claim 4, comprising a planetary transmission having a driven shaft supported in the rear plate and a drive shaft supported in the front plate, a mounting structure arranged on the drive shaft for a force transmitting engagement of the drill needle, a gear mounted on the driven shaft projecting rearwardly from the carriage wherein the gear engages a drive gear supported on the rear plate, the gear having a center opening through which the main shaft extends so as to drive said gear while the carriage is moved back and forth, the gear and the drive gear having axes disposed at a given distance but being exchangeable by different diameter gears such that the transmission ratio is variable, support plates which consist of thin metal sheets or plastic plates arranged in front of the carriage in the slide path thereof on the slide bars and having an opening along the drill axis, through which opening the drill needle is guided, said support plates being moved together to a thin packet when the carriage advances and being pulled apart again to their original position by thin plastic strings when the carriage returns.

7. A drill resistance measuring apparatus according to claim 6, wherein said variable transmission includes cassettes which have differently grouped gear sets and which are easily exchangeable for changing the transmission ratio.

8. A drill resistance measuring apparatus according to claim 7, wherein said means for plotting includes an arrangement comprising the following design features: the planetary transmission is pivotally supported on the front and rear plates of the carriage by way of its driven shaft and its drive shaft, the housing of the planetary transmission is connected, by way of a tension spring, with a spring tensioning device firmly mounted to the carriage, the housing of the planetary transmission carries, on a bent holder, a pen in such a way that the pivot movement thereof is plotted on a tablet disposed in said tubular body portion for plotting the pivoting of the housing of the planetary transmission, which depends on the varying drill resistances.

9. A drill resistance measuring apparatus according to claim 8, wherein a flap window is disposed on the top of the drill attachment under which said tablet is arranged for receiving a plotting device extending over the full length of the carriage.

10. A drill resistance measuring apparatus according to claim 9, wherein the plotting device includes a sheet or a card cut to the appropriate length or unrolled from a roll.

11. A drill resistance measuring apparatus according to claim 1, wherein said drive unit is an electrically operated hand drill.

* * * * *